United States Patent
Shoham

(10) Patent No.: US 10,058,338 B2
(45) Date of Patent: *Aug. 28, 2018

(54) MINIATURE BONE-ATTACHED SURGICAL ROBOT

(75) Inventor: Moshe Shoham, Hoshaya (IL)

(73) Assignee: MAZOR ROBOTICS LTD., Caesarea (IL)

( * ) Notice: Subject to any disclaimer, the term of this patent is extended or adjusted under 35 U.S.C. 154(b) by 342 days.

This patent is subject to a terminal disclaimer.

(21) Appl. No.: 12/725,487

(22) Filed: Mar. 17, 2010

(65) Prior Publication Data

US 2010/0204714 A1  Aug. 12, 2010

Related U.S. Application Data

(63) Continuation of application No. 10/965,100, filed on Oct. 15, 2004, now abandoned, which is a
(Continued)

(51) Int. Cl.
*A61B 34/30* (2016.01)
*A61B 17/17* (2006.01)
(Continued)

(52) U.S. Cl.
CPC .......... *A61B 17/1757* (2013.01); *A61B 6/583* (2013.01); *A61B 34/30* (2016.02);
(Continued)

(58) Field of Classification Search
CPC ............ A61B 17/1757; A61B 17/1703; A61B 17/171; A61B 17/1695; A61B 2019/208; A61B 2019/2207; A61B 2019/2223; A61B 2019/2249; A61B 2019/501; A61B 2019/507; A61B 19/52; A61B 2019/5289; A61B 2019/5291–2019/5297; A61B 90/10; A61B 90/14; A61B 34/00; A61B 34/10; A61B 34/20; A61B 34/30; A61B 34/32; A61B 34/35; A61B 34/70; A61B 34/72; A61B 5/066; A61B 5/5229; A61B 6/484; A61B 6/485; A61B 6/486; A61B 6/487; A61B 6/488; A61B 6/4417; A61B 6/5217; A61B 6/5235; A61B 6/5247; A61B 6/5252; A61B 19/20; A61B 19/22; A61B 19/26; A61B 19/50; A61B 19/5225;
(Continued)

(56) References Cited

U.S. PATENT DOCUMENTS 4,791,934 A * 12/1988 Brunnett ................ 600/429
4,979,949 A * 12/1990 Matsen et al. ............ 606/53
(Continued)

OTHER PUBLICATIONS

Brack, C. et al., Accurate X-Ray-based Navigation in Computer-Assisted Orthopedic Surgery, Computer Aided Radiology and Surgery, Elsevier Science B.V., p. 716-722 (1998).*
(Continued)

*Primary Examiner* — Katrina Stransky
*Assistant Examiner* — Erin Colello
(74) *Attorney, Agent, or Firm* — Daniel Feigelson; Fourth Dimension IP

(57) ABSTRACT

Disclosed are methods for performing a surgical procedure at a surgical site utilizing a surgical robot. Other embodiments are also disclosed.

23 Claims, 5 Drawing Sheets

Related U.S. Application Data continuation of application No. 09/912,687, filed on Jul. 24, 2001, now Pat. No. 6,837,892.

(60) Provisional application No. 60/220,155, filed on Jul. 24, 2000.

(51) Int. Cl.
 *A61B 6/00* (2006.01)
 *A61B 34/00* (2016.01)

(52) U.S. Cl.
 CPC .............. *A61B 34/70* (2016.02); *A61B 34/72* (2016.02); *A61B 2034/742* (2016.02); *Y10T 74/20305* (2015.01)

(58) Field of Classification Search
 CPC . A61B 19/201; A61B 19/203; A61B 19/2203; A61B 2090/101; A61B 2034/742; A61B 2034/2065; A61B 2034/107; A61B 2576/00; A61B 2019/223; G06K 9/6203; Y10T 74/20305; G06T 2207/30004; G06T 2207/30008; G06T 2207/30012; G06T 3/30; G06T 3/0012; G06T 3/0068
 USPC .................. 606/130; 600/417, 421, 427, 429
 See application file for complete search history.

(56) References Cited

U.S. PATENT DOCUMENTS

| | | | |
|---|---|---|---|
| 5,230,338 A * | 7/1993 | Allen et al. .................... 600/429 |
| 5,300,080 A * | 4/1994 | Clayman et al. ............. 606/130 |
| 5,383,454 A * | 1/1995 | Bucholz ........................ 600/429 |
| 5,682,886 A | 11/1997 | Delp et al. |
| 5,695,501 A * | 12/1997 | Carol ..................... A61B 19/20 600/414 |
| 5,752,962 A * | 5/1998 | D'Urso .......................... 606/130 |
| 5,769,078 A * | 6/1998 | Kliegis .......................... 600/407 |
| 5,799,055 A * | 8/1998 | Peshkin ................. A61B 6/464 378/42 |
| 5,824,085 A * | 10/1998 | Sahay ................. A61F 2/30942 128/898 |
| 5,871,018 A | 2/1999 | Delp et al. |
| 5,891,034 A * | 4/1999 | Bucholz ........................ 600/426 |
| 5,951,475 A * | 9/1999 | Gueziec ................ G06T 3/0068 128/922 |
| 5,963,612 A | 10/1999 | Navab |
| 5,993,463 A * | 11/1999 | Truwit .......................... 606/130 |
| 6,009,212 A | 12/1999 | Miller et al. |
| 6,049,582 A | 4/2000 | Navab |
| 6,069,932 A | 5/2000 | Peshkin et al. |
| 6,096,050 A * | 8/2000 | Audette ........................ 606/130 |
| 6,118,845 A | 9/2000 | Simon et al. |
| 6,167,292 A * | 12/2000 | Badano et al. ............... 600/407 |
| 6,198,794 B1 | 3/2001 | Peshkin et al. |
| 6,226,548 B1 * | 5/2001 | Foley et al. .................. 600/426 |
| 6,236,875 B1 * | 5/2001 | Bucholz et al. ............. 600/407 |
| 6,246,898 B1 * | 6/2001 | Vesely ................. A61B 5/0422 600/424 |
| 6,298,262 B1 | 10/2001 | Franck et al. |
| 6,301,495 B1 * | 10/2001 | Gueziec ................... A61B 6/00 600/407 |
| 6,314,310 B1 * | 11/2001 | Ben-Haim ............. A61B 19/52 600/424 |
| 6,322,567 B1 * | 11/2001 | Mittelstadt ............. A61B 34/70 606/130 |
| 6,347,240 B1 * | 2/2002 | Foley .................... A61B 5/0064 600/426 |
| 6,348,058 B1 * | 2/2002 | Melkent et al. .............. 606/130 |
| 6,359,960 B1 | 3/2002 | Wahl et al. |
| 6,370,224 B1 | 4/2002 | Simon et al. |
| 6,416,520 B1 * | 7/2002 | Kynast et al. ................ 606/130 |
| 6,442,417 B1 * | 8/2002 | Shahidi ................. A61B 90/36 600/117 |
| 6,470,207 B1 * | 10/2002 | Simon ..................... A61B 6/463 378/207 |
| 6,490,467 B1 * | 12/2002 | Bucholz et al. ............. 600/407 |
| 6,490,475 B1 * | 12/2002 | Seeley ..................... A61B 5/06 378/21 |
| 6,529,765 B1 * | 3/2003 | Franck .................. A61B 90/10 600/427 |
| 6,546,277 B1 * | 4/2003 | Franck .................. A61B 90/10 600/426 |
| 6,676,669 B2 * | 1/2004 | Charles et al. .............. 606/130 |
| 6,711,432 B1 * | 3/2004 | Krause ................... A61B 17/15 128/922 |
| 6,778,850 B1 * | 8/2004 | Adler ....................... A61B 6/12 378/4 |
| 7,327,872 B2 * | 2/2008 | Vaillant .................. A61B 6/032 382/128 |
| 2001/0021806 A1 * | 9/2001 | Gueziec ................ A61B 6/032 600/425 |
| 2002/0029045 A1 * | 3/2002 | Bonutti ............................ 606/86 |
| 2002/0049377 A1 * | 4/2002 | Moctezuma De La Barrera et al. ............................ 600/407 |
| 2002/0087101 A1 * | 7/2002 | Barrick ................ A61B 5/1077 600/587 |
| 2003/0009169 A1 * | 1/2003 | Young et al. ................... 606/86 |
| 2004/0116906 A1 * | 6/2004 | Lipow .............................. 606/1 |

OTHER PUBLICATIONS

Hamadeh, All et aL., Automated 3-Dimensional Computed Tomographic and Fluoroscopic Image Registration, Computer Aided Surgery 3:11-19 (1998).*

Hamadeh, All et al., Towards automatic registration between CT and X-ray images: cooperation between 3D/2D registration and 2D edge detection, Medical Robotics and Computer Assisted Surgery, p. 39-46 (1995).*

Murphy, Martin J., An automatic six-degree-of-freedom image registration algorithm for image-guided frameless stereotaxic radiosurgery, Med. Phys.. 24 (6), p. 857-866 (1997).*

Davies, B., et al. "Neurobot: a special-purpose robot for neurosurgery." Robotics and Automation, 2000. Proceedings. ICRA'00. IEEE International Conference on. vol. 4. IEEE, 2000.*

Guéziec, André, et al. "Anatomy-based registration of CT-scan and intraoperative X-ray images for guiding a surgical robot." Medical Imaging, IEEE Transactions on 17.5 (1998): 715-728.*

* cited by examiner

MINIATURE BONE-ATTACHED SURGICAL ROBOT

This Application is a continuation of co-pending application Ser. No. 10/965,100, filed Oct. 15, 2004, which is a continuation of application Ser. No. 09/912,687, filed Jul. 24, 2001, now U.S. Pat. No. 6,837,892, which claims priority from Provisional Application Ser. No. 60/220,155, filed Jul. 24, 2000. The contents of all of the above-listed applications are incorporated herein by reference.

TECHNICAL FIELD

The present invention relates to a robotic device. Particularly, this invention relates to a robotic device that attaches to a bone of the patient and aids or performs surgical procedures.

BACKGROUND OF THE INVENTION

Generally, robots are used in many different industries for many different applications. One industry, for example, is the medical industry that uses robots in applications including assisting the surgeon during surgical procedures. Robots are especially suited for some surgical tasks because they can be constructed to be very steady, computer controlled, and precise in their movements. Characteristics such as these can be especially helpful during surgery on sensitive areas, such as, for example, the vertebral column but are applicable throughout the body.

Typical vertebral column surgical procedures include vertebral fusion, insertion of medical devices such as pedicle screws, discography, percutaneous discectomy, or the like. These procedures typically require a large invasive operation that exposes the patient to a high risk of infection, excessive trauma, fluid loss, post operative pain, scarring, and a lengthy recovery time. Some difficulties relating to surgery on the vertebral column include micro-movement of the vertebral column during the operation, inherently small target objects of the procedure such as the pedicles, extremely delicate nearby nerve tissue, and limited operating room space because large equipment is needed to aid in the procedure, such as C-arm X-ray devices. Furthermore, the patient and operating room staff are exposed to large doses of radiation because these procedures require repeated X-raying and/or fluoroscoping of the surgical site so the surgeon can view the position of surgical tools or implants relative to non-visible body parts.

A need exists for a device that can assist minimally invasive surgery with low radiation exposure while allowing the surgeon to precisely align and control or monitor the surgical procedure. Some prior art devices have attempted to accomplish this however, these devices are either too complicated, not sufficiently accurate, or consume too much operating room space.

One such device is disclosed in U.S. Pat. No. 6,226,548. This device combines a navigation system, a bone mounted apparatus, and surgical tools that communicate with the navigation system. This apparatus primarily consists of a clamp that attaches to the patient's spine and extends outward forming a reference are bearing emitters or a tracking means. All the surgical tools used in this procedure are fitted with emitters or a tracking means similar to the reference arc. The surgical suite is fitted with a navigation system capable of recognizing the emitters or tracking means of the reference arc and surgical tools, a computer system for interpreting the location of the tools, and a video display for the surgeon. After surgically placing the clamp and reference arc on the patient a CT or MRI is taken creating a three-dimensional image of the patient with the attached device. When the patient is in place in the surgical suite with the attached reference arc the navigation system locates the arc and the surgical tools and displays them, relative to each other, on the three-dimensional CT scan.

While the device disclosed in the '548 patent offers some advantages in terms of accuracy and reduced trauma, the advantages of this type of prior art device are limited. The critical part of a surgical tool that must be monitored is the working end of the tool, whether that be a screwdriver or a drill bit or the like. These cannot be tracked with such prior art systems. Transmitters or emitters cannot be attached to the working ends of tools so the computer must estimate the location of the working end by locating the tool generally and extrapolating. This causes inaccuracy and errors that cannot be tolerated in spinal surgery or other high accuracy procedures where the smallest error can result in a serious and permanent outcome. Also, prior art devices such as these are hand held by the surgeon and thus, limited in accuracy to the surgeon's ability to hold and align the tool.

Furthermore, when using this system, the user must be cautious to not block the line-or-sight between the tool mounted emitters or receivers, the reference arc bearing emitters or receivers, and the navigation system. This can severely limit the ability of the surgeon or surgical team as the tool may actually limit their ability to aid the patient. Also, while such prior art systems do reduce the incision size, they complicate the surgical procedure. Usually a patient is brought into a surgical suite ready for a procedure, the procedure is performed, completed, and the patient leaves. However, the '548 patent system requires the patient to be put through a surgical procedure to affix the clamp and referencing arc, then the patient is transported to a CT or MRI, then transported back to the surgical suite in a non-sterile condition for the substantial portion of the procedure to commence. Finally, this system has many components, such as the navigation system and the computer output unit, that clutter up the already limited space in the surgical suite.

Therefore, there is a need in the art for a device with high precision and accuracy that can assist the surgeon in aligning the working end of the surgical tool such that delicate procedures can be preformed percutaneously with minimal radiation exposure to both the patient and the surgical staff.

SUMMARY OF THE INVENTION

The present invention is directed to a device and method for assisting in surgical procedures. According to the invention, a robot is disclosed that precisely positions a surgical tool with respect to a surgical site. The robot attaches to the bone of a patient with a clamp or with wires such as K-wires. Actuators extend from the robot base and move away from and toward the base member. This manipulates balls that rotate within spherical swivel joints that in turn align a sleeve. A surgical tool such as a screw driver or a drill bit is inserted through the sleeve and thus is precisely aligned with a site requiring surgery.

The present invention also includes a method for using the robot to assist in surgical procedures. Initially, three dimensional images are taken of the patient and the surgeon performs pre-operative planning of the procedure to be done on the images. This creates parameters that will later be used to direct the robot to the location where the surgical procedure is required. The robot is then attached to the patient by the clamp or the k-wire. C-arm images are taken of the patient with the attached clamp and these images are co-registered and calibrated such that a precise image of the bone with the robot attached is generated. This image is then registered, or matched, with the three dimensional image. This is accomplished in a highly efficient and accurate manner by taking small windows of the images where the surgery is to take place and registering these small portions. The small windows are chosen off the images by locating the bone attached clamp and selecting a window according to pre-operative calculation of the bone-robot attachment location. After these windows are chosen and registered, the remaining bone is registered by aligning the registered windows. At this point the robot is located precisely on the bone of the patient in the three dimensional image and can be manipulated by the surgeon to a pre-operative planned location for percutaneous insertion of surgical tools, medical devices, or implants.

BRIEF DESCRIPTION OF THE DRAWINGS

For a better understanding of the nature, objects, and function of the present invention, reference should be made to the following detailed description in conjunction with the accompanying drawings, in which.

Like reference numerals refer to corresponding elements throughout the several drawings.

DETAILED DESCRIPTION OF THE PREFERRED EMBODIMENT

Figure 1:
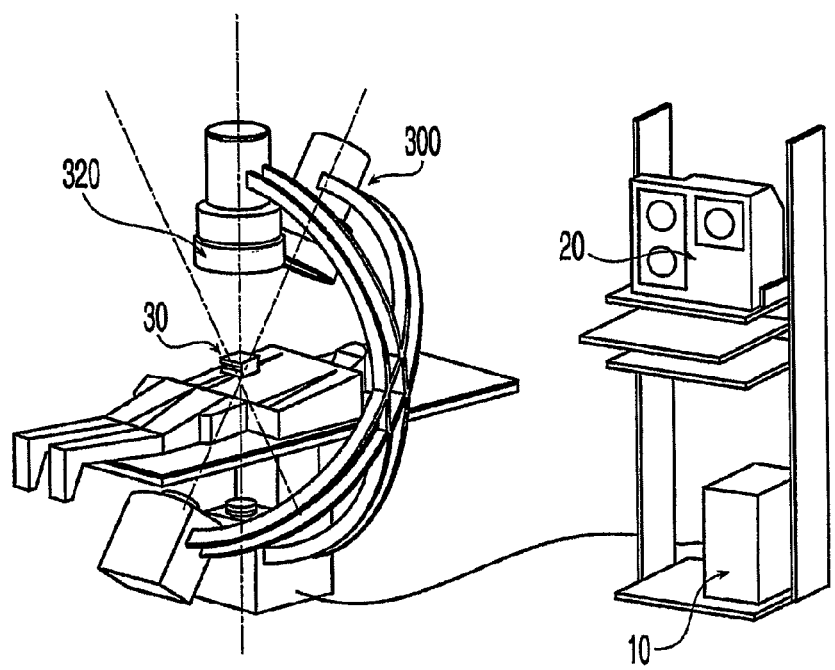
FIG. 1 is an overview of an embodiment of a surgical system showing a control unit with a display, C-arm with a calibration phantom attached, and a robot used for aligning surgical tools attached to the patient according to the present invention.

Referring to the illustrations and particularly to FIG. 1 it can be seen that a preferred embodiment of the present invention generally includes an image guided, robot assisted, surgical system. Included in this system generally, as shown in FIG. 1, is a bone attached surgical robot 30; a control unit 10 that matches data from CT scans and C-arm images to locate robot 30 on the patient's bone and allows a surgeon to control robot 30, through the use of a mouse, joystick, touch screen, or the like; and video display 20. Control unit 10 generally includes a cpu and user interface communicating with display 20 and robot 30.

Figure 2:
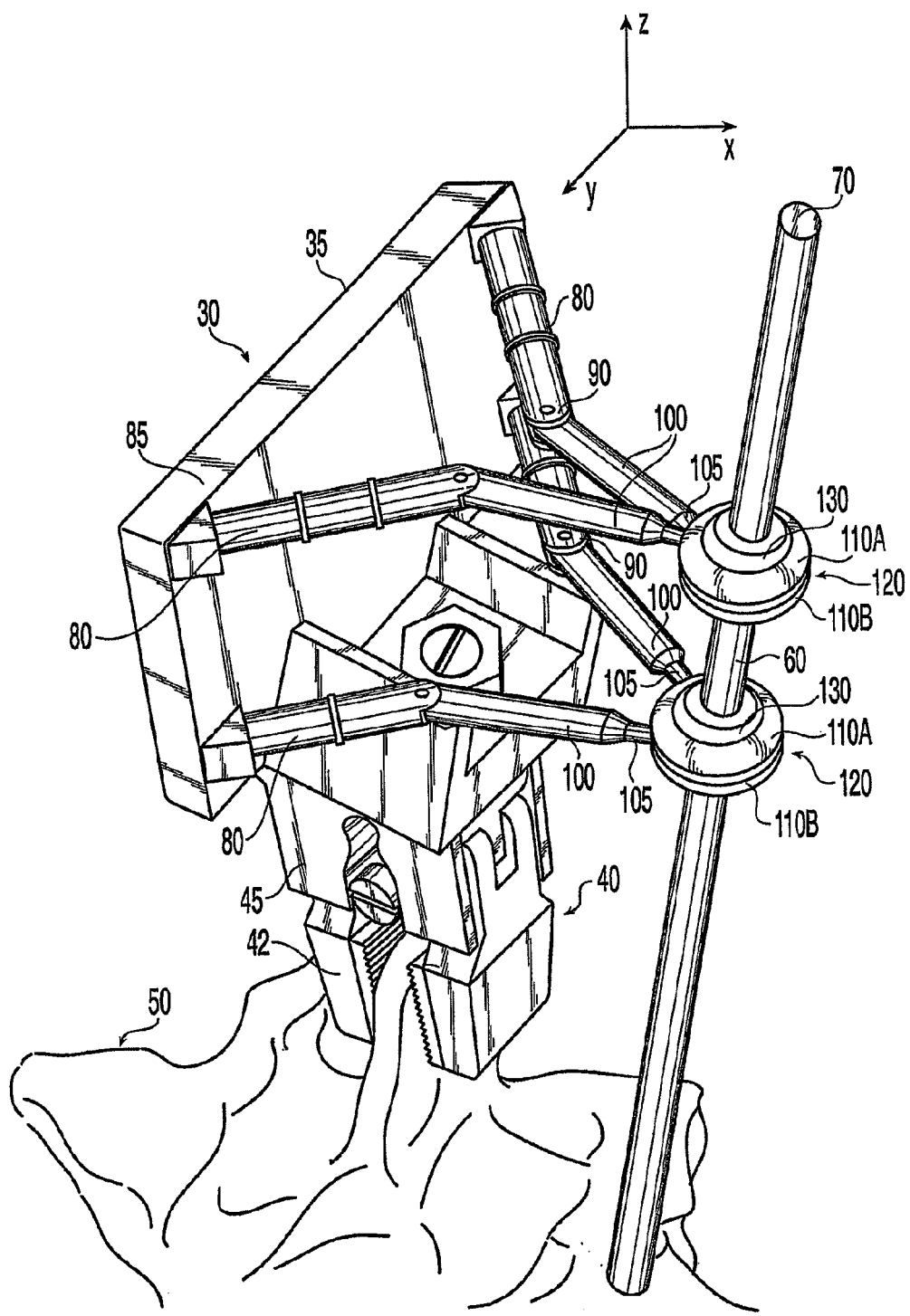
FIG. 2 is a perspective view showing a miniature surgical robot attached to a bone and aligning a surgical tool in an embodiment of the invention.

FIG. 2 illustrates robot 30 according to one embodiment of the present invention attached with clamp 40 to vertebra 50. Robot 30 aligns sleeve 60 through which surgical tool 70 such as a screwdriver, drill bit, Kirschner wire (K-wire), or the like can be inserted and precisely aligned with a site requiring a surgical procedure and thus, the operation can be conducted percutaneously or in traditional open procedures.

In a preferred embodiment of the invention, robot 30 includes base 35 that sits vertically on clamp adaptor 45. At least two pairs of actuators 80 extend from base 35. The actuators 80 extend from the base 35 forming a fixed angle 85 between base 35 and actuator 80. This angle is generally between about 15-90 degrees and more preferably about 45 degrees. In one preferred embodiment, the points of attachment of actuators 80 are spaced apart by about 50 mm in the Z direction and about 50 mm in the Y direction. Each actuator 80 is capable of operating independently from the other actuators 80. Actuator 80 is similar to known linear actuators and includes a housing, a motor, a lead screw, an electrical connection, and a position sensor such as an optical encoder, an LVDT, or the like. In a preferred embodiment each actuator is approximately 5 mm in diameter and approximately 35 mm in length.

The end of actuator 80 that is not fixedly attached to base 35 contains hinge joint 90. Hinge joint 90 links actuator 80 to rigid member 100. In a preferred embodiment member 100 is about 4 mm in diameter and 40 mm in length. Hinge joint 90 permits member 100 to freely rotate through about 270 degrees on an axis that runs parallel to base 35. The other end of the rigid member 100 is fixed with solid connection 105 to ring member 110. There is no movement between rigid member 100 and ring member 110 at solid connection 105.

Upper ring member 110A and lower ring member 110B, solidly connected to individual rigid members 100, come together at spherical swivel joint 120. Each ring member 110 forms one half of an outer race of spherical swivel joint 120. Ring members 110 are free to rotate with respect to one another, but are held fixedly from separating in the Z axis direction. Contained between upper ring member 110A and lower ring member 110B, and free to swivel, is ball 130. Passing through ball 130 is sleeve 60. Sleeve 60 passes through both upper and lower balls 130, forming an aligning axis through which surgical tool 70 is passed. As actuators 80 extend and retract, hinge joints 90 freely rotate about the Z axis and balls 130 swivel in the spherical swivel joints 120 formed by upper and lower ring members 110. A hollow axis is formed by the sleeve passing through each of upper and lower balls 130 such that a surgical tool 70 can be inserted through and be accurately aligned with the working location.

According to the present invention the above described robot 30 is just one example of a robot configured for surgical assistance that may be utilized with the system according to the present invention. Other robot configurations that could satisfy the same tasks include, for example, a parallel robot constructed to the required dimensions, such as that described in Simaan, N., Glozman, D., and Shoham, M.: "Design Considerations of new types of Six-Degrees-of-Freedom Parallel Manipulators," IEEE International Conference on Robotics and Automation, Belgium, 1998, which is incorporated by reference herein.

Figure 3:
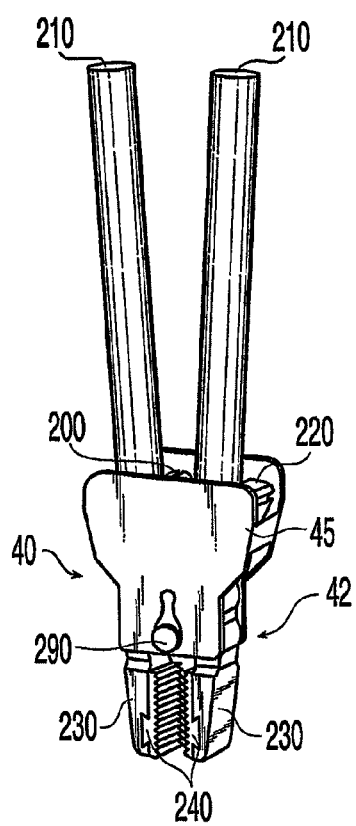
FIG. 3 is a perspective view showing a clamp for attaching to a bone and adaptor for receiving a robot in an embodiment of the invention.
Figure 4:
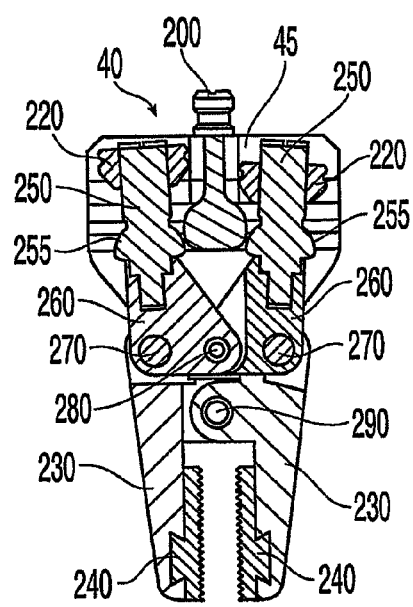
FIG. 4 is a cross-sectional view of FIG. 3.

In a preferred embodiment of the invention, robot 30 is attached with the bone of a patient by clamp 40. As shown in FIGS. 3 and 4, clamp 40 comprises bone clamping portion 42 and clamp adaptor 45. Initially, handles 210 extend from clamp 40 and allow a user to hold, align, and affix clamp 40 onto a bone of the patient. The base of the handles 210 fit over nuts 220, shown in FIG. 4, located on clamp 40. When clamp 40 is in place, the user pushes handles 210 toward each other to close jaws 230 onto the selected bone. When handles 210 are fully closed, or pushed together, a first locking (described below) occurs and clamp 40 is locked in place on the bone. The user then rotates handles 210 in a clockwise direction, turning and tightening nuts 220. Nuts 220 tighten down on threaded studs 250 and pinch clamp adaptor 45 onto bone clamping portion 42. This causes a second locking of clamp 40 into place on the bone. The base of each threaded stud 250 has a spherical mating surface 255 so that when clamp adaptor 45 is tightened down onto bone clamping portion 42 the clamp adaptor can self align itself on spherical mating surface 255 of stud 250. This allows the top surface of clamp adaptor 45 to maintain a horizontal surface for receiving the robot base 35. The handles, 210, are then removed by pulling straight up and away from the clamp 40. Protruding from the top surface of clamp adaptor 45 are connection pins 200. Connection pins 200 align with receiving holes in robot base 35 and when inserted lock robot 30 into place by some type of a snap ring or spring and ball bearing or plunger ball/pin.

With reference specifically to FIG. 4, it can be seen that threaded studs 250 are embedded in levers 260. Left and right levers 260 are connected together by upper center hinge 280. The other end of levers 260 connect with respective jaws 230 through side axis hinge 270. Left and right jaws 230 are connected together by main pivot 290 around which the jaws rotate. When a user pushes handles 210 together to close jaws 230, upper center hinge 280 is pushed downward and at the same time side axis hinges 270 rotate around the main pivot 290. The first locking occurs when upper center hinge 280 is pushed below the center line formed between left and right side axis hinges 270, and clamp 40 locks onto the bone. When clamp 40 is in the fully closed and locked position, jaws 230 are parallel to each other and separated by a set distance. The set closing distance between jaws 230 can be altered for different bone attachment applications by exchanging re-moveable jaw inserts 240 with the same of a different thickness.

Figure 7:
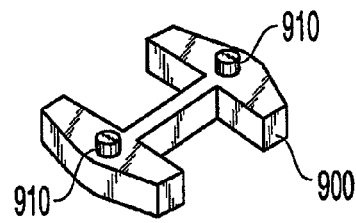
FIG. 7 is a perspective view of a spacer used to extend the clamp.

FIG. 7 illustrates spacer 900 that can be attached to the top surface of clamp adaptor 45 to ensure that robot 30 remains above the working area and out of any tissue that might occur when a patient has unusual body proportions. Spacer 900 attaches to connector pins 200 of clamp adaptor 45 and provides connector pins 910, similar to connector pins 200, for robot 30 attachment to the top surface of the spacer 900.

Figure 8:
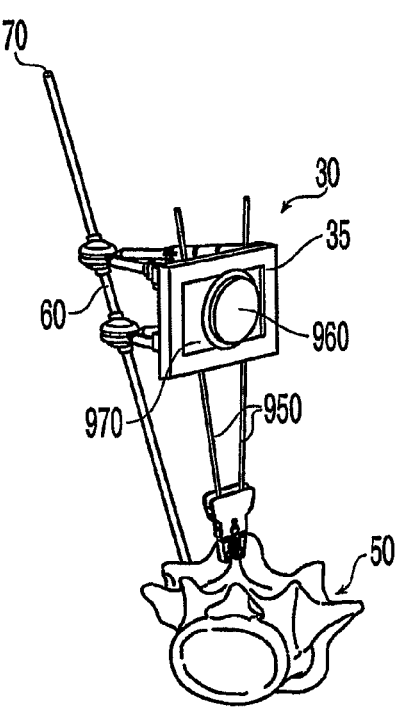
FIG. 8 is a perspective view showing a miniature surgical robot for aligning a surgical tool attached to a bone by K-wires in an embodiment of the invention.

Above described clamp 40 is an example of one embodiment according to the invention by which a robot may be attached to a bone for assisting in a surgical procedure. Other attachment devices can also be incorporated with a robot such as, for example, K-wire connections. FIG. 8 illustrates such a K-wire connection. K-wires 950 are inserted into the bone by standard surgical procedures. Robot base 35 contains an elongated slot through which K-wires 950 are inserted. Screw 960 can then be turned and tighten pinch plate 970 against robot base 35 pinching K-wires 950 between pinch plate 970 and robot base 35 holding robot 30 tight with respect to K-wires 950 and bone 50.

Figure 5:
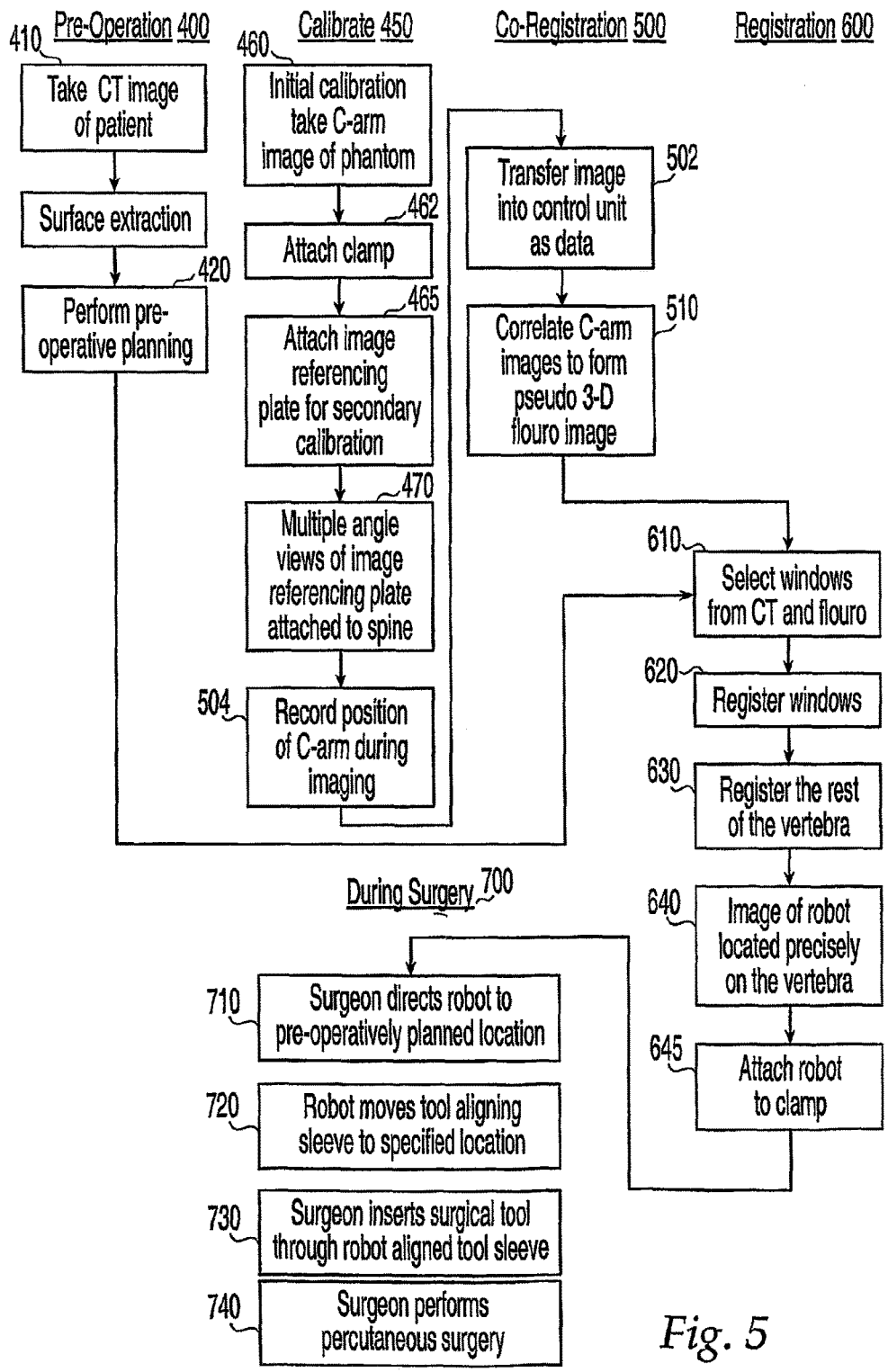
FIG. 5 is a flow chart of an embodiment of the method of using the present invention.

FIG. 5 illustrates the registration system used to establish the position of the robot on the bone. Initially there is a pre-operative step 400. This step 400 consists of taking a three-dimensional scan 410 of the patient, such as a CT or MRI scan. A surgeon then performs pre-operative planning 420 on the three-dimensional scan. For example, if the procedure to be done is a fracture fixation, the surgeon will study the three-dimensional image and the condition of the bone, choose the proper implant from a database containing implants of all types and sizes based on the present application, and electronically position and insert the implant, the screw, or the like. This is known in the art, for example, as described in "Marching Cubes: a high resolution 3D surface reconstruction algorithm", W. E. Lorensen, H. E. Cline, Computer Graphics 21 (1987) 163-169 which is incorporated by reference. The parameters generated by the pre-operative planning 420 are stored in the control unit 10 for positioning the robot 30 during the actual surgical procedure.

Figure 6:
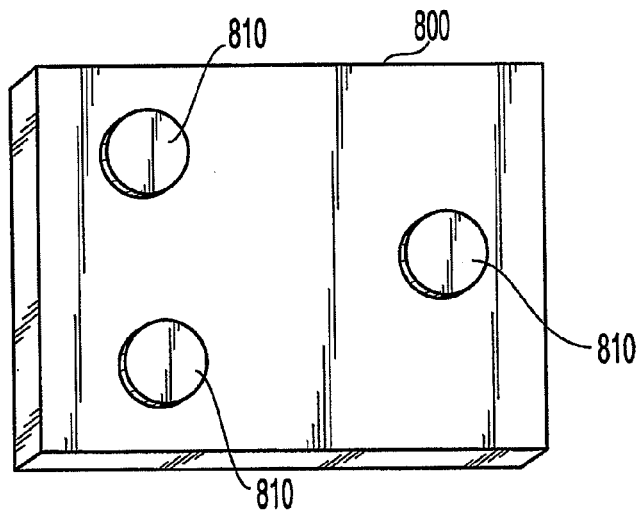
FIG. 6 is a perspective view of an image referencing plate with three referencing markers attached.

With reference now to FIGS. 1, 5, and 6 the next step is initial calibration of the C-arm 450. A phantom 320 (FIG. 1) is attached to the lens of the C-arm device 300 and a blank C-arm image is taken, step 460, FIG. 5. The phantom 320 is used to correct for the distortion associated with the C-arm image. The phantom contains several reference objects and a large number of small reference objects. The control unit automatically recognizes the reference objects and creates distortion correction maps and calibration intrinsic parameters to correct for the imprecise C-arm image. Systems such as these are known in the art and described, for example, in Brack et al., "Accurate X-ray Navigation in Computer-Assisted Surgery", Proc. Of the 12th Int. Symp On Computer Assisted Radiology and Surgery, H. Lemke, et al., eds., Springer, 1998; Yaniv et al., "Fluoroscopic Image Processing for Computer-Aided Orthopaedic Surgery", Proc. 1st Int. Conf. On Medical Computing and Computer-Assisted Intervention, Lecture Notes in Computer Science 1496, Elsevier, et al., eds., 1998; Hofstetteret al., "Fluoroscopy Based Surgical Navigation—Concept and Clinical Applications", Proc. 11th Int. Symp. on Computer Assisted Radiology and Surgery, H. U. Lemke, et al., eds., Springer 1997; Tsai, R., "A Versatile Camera Calibration Technique for High-Accuracy 3D Machine Vision Metrology Using Off-the-Shelf TV Cameras and Lenses", IEEE Journal of Robotics and Automation, Vol. RA-3,No. 4, August 1987, which are incorporated by reference.

Next, the patient is brought into the operating room, a small incision is made according to standard surgical practice at the site where clamp 40 is to be attached, and the clamp is attached to the selected bone using handles as described above, step 462, FIG. 5. Handles 210 are then removed from the clamp 40. An image referencing plate 800 (FIG. 6) is attached to clamp 40, step 465, FIG. 5, by receiving holes that receive connector pins 200. The image referencing plate 800 (FIG. 6) has three referencing markers 810 on it that show up very clear and precise in the C-arm image. The distance and angle between the referencing markers 810 are known such that the C-arm image can be calibrated in a secondary calibration step, step 465, to accurately represent actual size of the image. At least two, but preferably three C-arm images are taken of the patient with the attached clamp 40 and image referencing plate 800. These C-arm images are taken from different angles, preferably 0, 45, and 90 degrees, step 470, FIG. 5.

In another embodiment of the present invention the secondary calibration step, step 465B, can be accomplished by attaching the robot 30 to the clamp and taking multiple C-arm images. By knowing the dimensions, or by placing referencing markers on robot 30 and knowing the distance and angle between the referencing markers the C-arm images can be calibrated in a secondary calibration step, step 465B.

The next step of the process is co-registration, step 500. The C-arm images are transferred into the control unit 10 as data, step 502. At each location an image is taken from, the position of the C-arm is recorded, step 504, into the control unit 10. The data of the images, step 502, and the position of the C-arm, step 504, are correlated by knowing the position from which each images was taken, step 504, and by aligning the referencing markers 810 (FIG. 6) from the image referencing plate 800 (FIG. 6). Thus, an accurate, pseudo three-dimensional image of the surgical site with the clamp 40 attached to the bone is generated. This stage can be referred to as robot to bone registration or co-registration.

According to a preferred embodiment of the invention, bone to bone registration next occurs in step 600. Step 600 is a process of estimating and matching the true surface contours or the objects in the images. Registration methods are either based on geometry or intensity of the image. Geometric based registration is achieved by finding features in the 2D fluoroscopic images and matching these features with corresponding features in the 3D image, acquired, for example, from a CT scan dataset, MRI image, ultrasound image or from a CAD model. The features can be known landmarks (anatomical landmarks or implanted fiducials), or contour points in the fluoroscopic image, matched with the registered object's surface. An algorithm that may be used to compute the transformation is the Iterative Closest Point (ICP) algorithm. This algorithm is described, for example in Besl, P. J. and McKay, N. D., "A Method for Registration of 3D Shapes", IEEE Trans. on Pattern Analysis and Machine Intelligence, 1992, 14(2), 239-255, which is incorporated herein by reference. The input to the algorithm are sets of back-projected rays from the fluoroscopic images, and a model of the registered object. The algorithm iteratively computes a transformation that approximates the ray sets to the model. For landmark registration, a match between each ray and the corresponding landmark is defined before searching for the transformation. Contour registration selects a new surface point to match with each ray on every iteration.

Preferably, the registration process uses two or more fluoroscopic images, as described in greater detail, for example, in Hamadeh, et al., "Towards automatic registration between CT and X-ray images: cooperation between 3D/2D registration and 2D edge detection", Medical robotics and computer assisted surgery, 1995, Wiley 39-46, and Hamadeh, et al., "Automated 3-Dimensional Computed Tomographic and Fluoroscopic Image Registration", Computer Aided Surgery, 1998, 3, which are incorporated herein by reference. According to this method, anatomical landmarks in the images are detected and matched manually. Based on this match, an approximated initial guess is computed, with ray intersections, which are 3D points in the registration environment, being matched with the model's landmarks. Then, the object's contour in the 2D image is registered with the model's surface. A likelihood estimator is used to remove outliers, or pixels not in the contour, from the sample point set. A signed distance function is defined to overcome any internal contours problems. The overall in-vitro accuracy of this method can be better than 2 mm.

In one alternative, a single fluoroscopic image may be used for registration, achieving an accuracy of about 3 mm. This technique is based on a combinatorial search among matches of three points and three rays. The match with minimal average distance for the registration is then selected. This alternative is described in Tang, "Method for Intensity-based Registration with CT Images," Masters Thesis: Department of Computer Science, Queen University, Ontario Canada, 1999, which is incorporated herein by reference.

In a further alternative according to the invention, intensity-based registration is achieved by comparing fluoroscopic images with simulated X-rays (digitally reconstructed radiographs, or DRR's) from an estimated position. Such a technique is generally described in Lemieux et al., "Patient-to computed-tomography image registration method based digitally reconstructed radiographs", Medical Physics, 21, 1994, 1749-1760 and Murphy, M. "An automatic six-degree-of freedom image registration algorithm for image-guided frameless stereotactic surgery", Medical Physics, 24(6), Jun. 1997, which are incorporated by reference herein.

When the camera position guess and the actual position are very close, the original and reconstructed image are very similar. Pixel intensity information is used to define a measure of similarity between the datasets. The similarity measure can include intensity values, cross-correlation, histogram correlation, and mutual information. The algorithm proceeds in three steps. The input is a CT data set, intrinsic camera parameters, one or more fluoroscopic images and an initial camera position estimate for each image. In the first step, the algorithm generates one DRR for each given camera position. In the second step, a dissimilarity measure is computed between the real and reconstructed image. In the third step, new camera poses are computed that best reduce the dissimilarity between the images. The process is repeated until convergence is reached. The parametric space of camera positions in then searched incrementally from an initial configuration. The space is six-dimensional (three rotations and three translations). The advantages of this technique is that no segmentation is necessary. However, the search space is six-dimensional, and can contain many local minima.

A benefit of the present invention is that it can utilize either of the above described registration methods. By utilizing the dimensions of the bone attached robot and its attachment location, the initial location of the window is a very good guess of the location and therefore the intensity based method can be utilized. Thus, according to the present invention, a faster and more accurate registration process is accomplished as between the fluorscopic and 3D images. This is done in step 600, and occurs very quickly and with a high degree of accuracy because the registration process is performed on small windows of the images, rather than the images as a whole. Preferably windows are selected that specifically relate to the known location of the robot and/or its support member. Windows of about 20 mm by 20 mm located approximately adjacent to the clamp location, according to pre-operative calculation of the bone-robot attachment location, are selected from the C-arm (fluoroscopic) image data, step 610. For example, these windows may be selected as the area above the attached clamp 40 in the C-arm image and the tip of the transverse process of the vertebra covering the area where the surgical procedure is to take place. Generally, the same windows are chosen from both the pseudo three-dimensional hybrid C-arm image, step 510, and also from the CT image (3D image), step 410. The small windows chosen from the C-arm images and the CT scan image are then laid over each other and matched or registered by the control unit, step 620, as described above. Focusing only on a small window of the C-arm image rather than looking for a matching anatomical landmark in the entire image, makes the process occur very fast and with the high degree of accuracy needed for precise procedures such as vertebra surgery.

Next, the remaining portion of the CT and C-arm image of the bones are overlaid, the registration windows are aligned, and the remaining bone is registered, step 630. Since the windows have already been accurately registered this step occurs quickly and also with a high degree of accuracy. Now clamp 40 is located precisely on the bone, step 640, of the CT image. Next, the user attaches robot 30 to clamp 40 and thus, robot 30 is located precisely with respect to the bone, step 645.

After robot 30 is co-registered 500 and registered 600, its position is known relative to the patient's bone and therefore can move to align with the pre-operatively picked location such that the operation can virtually take place on the control unit. The user selects a pre-operatively planned location and task from step 420 by use of a joystick, mouse, touch screen, or the like, step 710. The Robot 30 responds and moves sleeve 60 into position, step 720, such that when the user inserts a surgical tool 70 through the opening in the sleeve 60 the surgical tool 70 will be precisely aligned with the location requiring the surgical procedure, step 730. The surgeon can then insert a selected surgical tool 70 and operate without opening the surgical site to see the placement of the surgical tool because the surgeon can verify the positioning of the surgical tool 70 on the control unit 10 and display 20. Thus operating percutaneously or in general open procedures, with a high degree of accuracy, low trauma, small incisions, low chance of infection, and minimal exposure to radiation. A further benefit of this system is that because the robot is miniature it can be freely attached to the bone of a patient and move with the body. Therefore, the robot system does not need a dynamic referencing device to maintain orientation with the body once it is registered. This creates a more precise and less complicated system that is versatile and user friendly as the surgeon can manipulate the patient into different surgical positions without disturbing the robot system.

The present invention is illustrated herein by reference to a spinal vertebra attachment. However, it will be appreciated by those in the art that the teachings of the present invention are equally applicable to other bone attachments.

What is claimed is:

1. A system for performing at a surgical site a procedure planned using an initial image, said system comprising:
   a surgical robot;
   an attachment member configured and dimensioned to mount said surgical robot on a bone associated with said surgical site, such that said robot's position relative to said bone is unchanged with motion of said bone; and
   a controller adapted to process at least one intraoperative fluoroscopic X-ray image generated after attachment of said attachment member to said bone, such that said intraoperative image includes said surgical site and at least one of (i) said surgical robot, (ii) its attachment member, and (iii) a set of reference markers associated with either, such that a position of said robot is defined in said at least one intraoperative fluoroscopic X-ray image, said controller further adapted to use imaged anatomical features of said surgical site to register said initial image including said surgical site with said at least one intraoperative fluoroscopic X-ray image, whereby the position of said robot is registered in said initial image,
   wherein said controller is adapted to utilize said registration of said position of said robot to said initial image to align said robot relative to said surgical site, so that when the robot holds a surgical tool, the tool will be aligned to perform on said bone said procedure planned using said initial image.

2. A surgical system according to claim 1, wherein said controller adapted to direct said robot to align said surgical tool to perform on said bone said procedure planned using said initial image, without the need for a dynamic referencing device to maintain orientation of said robot relative to the position of said bone during said procedure.

3. A surgical system according to claim 1, wherein said robot is adapted to be controlled to align said surgical tool through use of at least one of a mouse, a joystick and a touch-screen.

4. A surgical system according to claim 1, wherein said surgical tool comprises at least one of a cutting member, a drilling member, a screwdriver, a drill bit and a Kirschner wire.

5. A surgical system according to claim 1, wherein said surgical tool is adapted to be carried in a surgical tool guide.

6. A surgical system according to claim 5, wherein said surgical tool guide is a sleeve adapted for insertion of said surgical tool.

7. A surgical system according to claim 1, wherein said robot is configured and dimensioned such that it can be fully supported on said bone.

8. A surgical system according to claim 1, wherein said attachment member is either one of a bone clamp or at least a pair of Kirschner-wires.

9. A surgical system according to claim 1, wherein said robot comprises a miniature parallel robot.

10. A surgical system of claim 1, wherein said robot comprises at least three actuators mounted on a base member, said actuators being configured for translational or rotational movement.

11. A surgical system according to claim 1, wherein said attachment member comprises a robot receiving adaptor mounted on a bone attachment portion.

12. A surgical system according to claim 11, wherein said bone attachment portion comprises either one of a clamp having at least two jaws shaped to clamp onto said bone or at least one wire configured and dimensioned to be received in a bone hole.

13. A method of performing a procedure at a surgical site, comprising:
   providing a surgical robot;
   providing an initial image including said surgical site, and using said initial image to plan said procedure;
   mounting said surgical robot on a bone associated with said surgical site, by means of an attachment member, such that said robot's position relative to said bone is unchanged with motion of said bone; and
   after attachment of said attachment member to said bone, generating at least one intraoperative fluoroscopic X-ray image including said surgical site and at least one of (i) said surgical robot, (ii) its attachment member, and (iii) a set of reference markers associated with either, such that the position of said robot is defined in said at least one intraoperative fluoroscopic X-ray image;
   using imaged anatomical features of said surgical site to register said initial image with said at least one intraoperative fluoroscopic X-ray image, such that the position of said robot is registered in said initial image; and
   utilizing said registration of said position of said robot to said initial image to align said robot relative to said surgical site so that when the robot holds a surgical tool, the tool is aligned to perform on said bone said procedure planned using said initial image.

14. A method according to claim 13, wherein said aligning of said robot is performed without the need for a dynamic referencing device to maintain orientation of said robot relative to the position of said bone during said procedure.

15. A method according to claim 13, wherein said aligning of said robot is performed by using at least one of a mouse, a joystick and a touch-screen.

16. A method according to claim 13, wherein said surgical tool comprises any one of a cutting member, a drilling member, a screwdriver, a drill bit and a Kirschner wire.

17. A method according to claim 13, wherein said surgical tool is carried in a surgical tool guide.

18. A method according to claim 17, wherein said surgical tool guide is a sleeve adapted for insertion of said surgical tool.

19. A method according to claim 13, wherein said robot is configured and dimensioned such that it can be fully supported on said bone.

20. A method according to claim 13, wherein said attachment member is either one of a bone clamp or at least a pair of Kirschner-wires.

21. A method according to claim 13, wherein said robot comprises a miniature parallel robot.

22. A system for performing at a surgical site a procedure planned using an initial image, said system comprising:
   a surgical robot;
   an attachment member configured and dimensioned to mount said surgical robot on a bone associated with said surgical site such that said robot's position relative to said bone is unchanged with motion of said bone; and
   a controller that processes adapted to process image including said surgical site and at least one of (i) said attachment member and (ii) a set of reference markers associated with said attachment member, but not including said robot, such that when said robot is mounted onto said attachment member, a position of said robot is defined in said at least one intraoperative fluoroscopic X-ray image, said controller further adapted to use anatomical imaged features of said surgical site to register said initial image including said surgical site with said at least one intraoperative fluoroscopic X-ray image, such that the position of said robot is registered in said initial image,
   wherein said controller is adapted to utilize said registration of said position of said robot to said initial image to align said robot relative to said surgical site, so that when the robot holds a surgical tool, the tool will be aligned to perform on said bone said procedure planned using said initial image.

23. A method of performing a procedure at a surgical site, comprising:
   providing an initial image including said surgical site, and using said initial image to plan said procedure;
   providing a surgical robot;
   providing an attachment member adapted to carry said robot in a predetermined position relative to said attachment member;
   mounting said attachment member on a bone associated with said surgical site, such that said attachment member's position relative to said bone is unchanged with motion of said bone;
   generating at least one intraoperative fluoroscopic X-ray image including said surgical site and at least one of (i) said attachment member, and (ii) a set of reference markers associated with said attachment member, such that the position of said attachment member is defined in said at least one intraoperative fluoroscopic X-ray image;
   following said generating of at least one intraoperative fluoroscopic X-ray image, mounting said robot on said attachment member such that the position of said robot is defined in said at least one intraoperative fluoroscopic X-ray image;
   using anatomical imaged features of said surgical site to register said initial image with said at least one intraoperative fluoroscopic X-ray image, such that the position of said robot is registered to said initial image; and
   utilizing said registration of said position of said robot to said initial image to align said robot relative to said surgical site so that when said robot holds a surgical tool, the tool is aligned to perform on said bone said procedure planned using said initial image.

* * * * *